United States Patent
Mittleman et al.

(10) Patent No.: US 9,689,853 B2
(45) Date of Patent: Jun. 27, 2017

(54) VISUAL BUFFERING ELEMENT FOR HAZARD DETECTOR INTERNAL COMPONENTS

(71) Applicant: GOOGLE INC., Mountain View, CA (US)

(72) Inventors: Adam Mittleman, Redwood City, CA (US); Mathias Schmidt, Emeryville, CA (US); Poll Shih, New Taipei (TW); William Dong, Palo Alto, CA (US); Nicholas Webb, Menlo Park, CA (US)

(73) Assignee: Google Inc., Mountain View, CA (US)

( * ) Notice: Subject to any disclaimer, the term of this patent is extended or adjusted under 35 U.S.C. 154(b) by 40 days.

(21) Appl. No.: 14/714,065

(22) Filed: May 15, 2015

(65) Prior Publication Data

US 2016/0334379 A1  Nov. 17, 2016

(51) Int. Cl.
*G01D 11/24* (2006.01)
*G08B 21/14* (2006.01)
*G01N 33/00* (2006.01)

(52) U.S. Cl.
CPC .................. *G01N 33/0036* (2013.01)

(58) Field of Classification Search
CPC ............................. G01D 11/245; G08B 21/14
USPC ......................................................... 73/431
See application file for complete search history.

(56) References Cited

U.S. PATENT DOCUMENTS

| | | | |
|---|---|---|---|
| 6,543,735 B1* | 4/2003 | Haynes | G08B 17/113 248/300 |
| 8,847,772 B2 | 9/2014 | Marks et al. | |
| 8,994,540 B2* | 3/2015 | Fadell | H04L 12/6418 340/628 |
| 9,349,273 B2* | 5/2016 | Fadell | H04L 12/6418 |
| 2012/0050030 A1* | 3/2012 | Murphy | G08B 17/107 340/514 |
| 2015/0097689 A1* | 4/2015 | Logue | G08B 25/10 340/632 |
| 2015/0100618 A1* | 4/2015 | Le Guen | G08B 25/10 709/201 |
| 2015/0194038 A1* | 7/2015 | Fadell | H04L 12/6418 340/517 |

* cited by examiner

*Primary Examiner* — Lisa Caputo
*Assistant Examiner* — Jamel Williams
(74) *Attorney, Agent, or Firm* — Kilpatrick Townsend & Stockton LLP

(57) ABSTRACT

A hazard detector includes a chassis configured to house components of the hazard detector. The chassis includes a front defining a central aperture. The front has a domed contour such that an outer edge of an inner portion extends beyond an outer periphery of the front. The inner surface tapers from the outer edge toward the inner portion. The detector includes a mesh formed to the contour of the front so the mesh is flat against the front. The mesh defines an aperture corresponding to the central aperture. The detector includes a grille secured to the chassis that defines an aperture corresponding to the central aperture and defines openings positioned along the grille. An inner surface of the grille includes a contour corresponding to the contour of the front so the mesh is flat against the inner surface. The mesh is positioned between the grille and the chassis.

20 Claims, 8 Drawing Sheets

VISUAL BUFFERING ELEMENT FOR HAZARD DETECTOR INTERNAL COMPONENTS

BACKGROUND OF THE INVENTION

In a structure, such as a house, various sensors may be mounted to the walls and ceilings. For example, carbon monoxide detectors and smoke detectors are two common types of sensors that are ubiquitous in households, offices, and other locations. While such sensors serve important safety functions, occupants of the structure also want to be surrounded by visually pleasing devices. These devices include many components that require exposure to the air, such as the carbon monoxide sensors. Additionally, the detectors include buzzers or other sound-generating components that are required to produce sufficiently loud sounds to be heard by people within the structure. As a result, the outer casing or grille of the detectors includes one or more apertures through which air and sound waves may pass. While functionally necessary, these apertures allow some or all of the interior components of the detector to be visible.

BRIEF SUMMARY OF THE INVENTION

In one aspect, a hazard detector is provided. The hazard detector may include a chassis configured to house components of the hazard detector. The chassis may include a front surface having an inner portion defining a chassis central aperture. The front surface may have a domed contour such that an outer edge of the inner portion extends beyond an outer periphery of the front surface. The inner surface may include a taper such that the outer edge tapers toward a center of the chassis to an inner edge of the inner portion. The hazard detector may also include a molded mesh. The molded mesh may be formed to match the domed contour of the front surface such that the molded mesh is substantially flat against the front surface. The molded mesh may define a mesh central aperture corresponding to the chassis central aperture. The hazard detector may also include a grille secured to the chassis. The grille may define a grille central aperture corresponding to the chassis central aperture and further defining a plurality of openings positioned along a body of the grille. An inner surface of the grille may include a domed contour corresponding to the domed contour of the front surface of the chassis such that the molded mesh is substantially flat against the inner surface. The molded mesh may be positioned between the front surface and the inner surface.

In another aspect, a method of securing a molded mesh to a chassis of a hazard detector is provided. The method may include aligning an adhesive backing of a mesh with a front surface of the chassis such that a chassis central aperture corresponds to a mesh central aperture and that a plurality of tabs formed radially around the mesh central aperture align with a tapered inner portion of the front surface. The front surface may include a domed contour such that an outer edge of the tapered inner portion extends beyond an outer periphery of the front surface. The inner portion may include a taper such that the outer edge tapers toward a center of the chassis to an inner edge of the inner portion. The method may also include flexing at least some of the plurality of tabs to conform to the tapered inner portion and adhering the at least some of the plurality of tabs to the tapered inner portion such that the mesh is secured to the chassis. The method may further include applying heat and pressure to the mesh to mold the mesh to conform to a three dimensional shape of the domed contour of the front surface and coupling a grille to the chassis, such that the mesh is disposed between the grille and the chassis.

In another aspect, a hazard detector may include a chassis configured to house components of the hazard detector. The chassis may include a contoured front surface. The hazard detector may also include a three dimensionally molded mesh secured to at least a portion of the contoured front surface. The three dimensionally molded mesh may conform to the contoured front surface such that the three dimensionally molded mesh is substantially flat against the contoured front surface. The three dimensionally molded mesh may include woven fibers having diameters between about 50 and 75 microns. The woven fibers may be spaced apart from one another by between about 100 and 200 microns such that the molded mesh has an air permeability of between about 5000 and 6500 $L/m^2s$ such that an audible signal of approximately 85 decibels may be emitted from the hazard detector that is audible at least 3 meters from the hazard detector and such that the molded mesh is penetrable by particulate matter detectable by the hazard. The hazard detector may further include a grille releasably secured to the chassis. The grille may define a plurality of openings positioned along a body of the grille. An inner surface of the grille may include a contour corresponding to the contoured front surface of the chassis.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

Figure 1A:
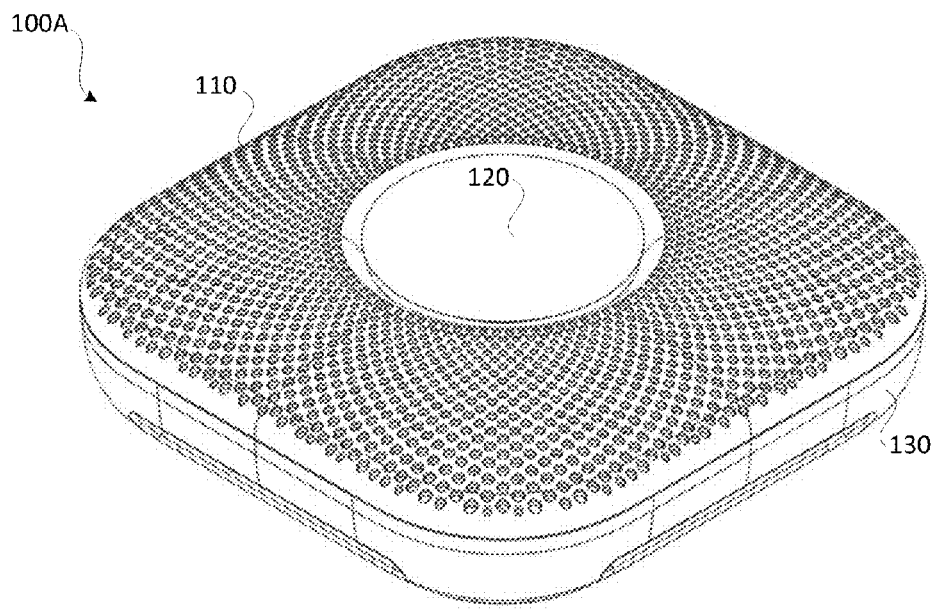
FIGS. 1A and 1B illustrate an embodiment of a smart combined smoke detector and carbon monoxide device.

A breathable, molded mesh or screen is presented that creates a consistent, visually pleasing appearance when placed against an interior surface of a cover grille and/or between a cover grille and a chassis of a smoke and carbon monoxide detector and/or other hazard detector, while still allowing carbon monoxide and/or other particulate within the air to pass through to sensors within the detector. The molded mesh may be used to create a uniform appearance for any type of hazard detector including, but not limited to, detectors for carbon monoxide, smoke, gas, other substances, and/or combinations thereof. Additionally, the mesh permits the detector to emit an alarm signal that is audible at least 3 meters from the detector at an intensity of at least 85 decibels. The dimensions of the mesh provide necessary porosity and acoustic properties, while disguising and/or otherwise covering up the appearance of internal components housed within the chassis. For example, without a mesh, components such as a speaker, a microphone, battery contacts, and other sensors may be visible through holes within the cover grille. The mesh is molded to conform to a contour shape of the chassis and cover grille. By being molded, the mesh may fit between the cover grille and chassis without folding, creasing, and/or otherwise bunching up. The molded maintains a consistent appearance, acoustic properties, fluid flow properties, and/or carbon monoxide, other particulate, and/or detectable substances to be admitted to the interior and/or sensors of the hazard detector.

In various embodiments detailed herein, a molded mesh is provided. The mesh may be formed from woven fibers to form a porous mesh that defines numerous apertures, through which carbon monoxide, smoke, and/or other particulate matter may pass while minimizing dampening of sound waves. The mesh may be formed from a material having a porosity selected such that an audible signal of approximately 85 decibels may be emitted from the hazard detector that is audible at least 3 meters from the hazard detector and such that the molded mesh is penetrable by carbon monoxide and/or other particulate matter.

In some embodiments, the molded mesh may define a central aperture that corresponds to a similar aperture of a chassis of a smoke and carbon monoxide detector. A plurality of flexible tabs may be formed radially around the central aperture. These tabs may be flexed or otherwise positioned to sit flush against a surface of the chassis without creases, other surface irregularities, or with minimal creases and/or irregularities. An adhesive may be provided to secure one, more than one, or all of the tabs to the chassis.

The mesh may be positioned between the chassis and a cover grille of the detector. The mesh may be molded such that the mesh has a profile formed to match the domed or other shaped contour of the front surface and/or a corresponding inner surface of the cover grille. As such, the molded mesh remains substantially flat against the interior of the front surface. This ensures that surface irregularities, such as creases, puckering, and the like are minimized and/or eliminated.

The following description focuses on the applications of various meshes. While discussed primarily within the context of a combination smoke and carbon monoxide detector, it should be understood that such meshes may be used for other hazard detectors and home appliance applications. For example, meshes may be used in a smoke detector, carbon monoxide detector, humidity sensor, ammonia sensor, other wall or ceiling mounted device, and/or combinations thereof.

FIG. 1A illustrates an angular top projection view of combined smoke detector and carbon monoxide device 100A. Device 100A may generally be square or rectangular and have rounded corners. Visible in the angular top projection view are various components of the combined smoke detector and carbon monoxide device 100A, including: cover grille 110, lens/button 120, and enclosure 130 (also referred to as sensor housing 130). Cover grille 110 may serve to allow air to enter combined smoke detector and carbon monoxide device 100A through many holes while giving device 100A a pleasing aesthetic appearance. Cover grille 110 may further serve to reflect light into the external environment of device 100A from internal lighting elements (e.g., LEDs). Light may be routed internally to cover grille 110 by a light guide, noted in relation to FIGS. 2A and 2C. It should be understood that the arrangement of holes and shape of cover grille 110 may be varied by embodiment. Lens/button 120 may serve multiple purposes. First, lens/button 120 may function as a lens, such as a Fresnel lens, for use by a sensor, such as an infrared (IR) sensor, located within device 100A behind lens/button 120 for viewing the external environment of device 100A. Additionally, lens/button 120 may be actuated by a user by pushing lens/button 120. Such actuation may serve as user input to device 100A. Enclosure 130 may serve as a housing for at least some of the components of device 100A.

Figure 1B:
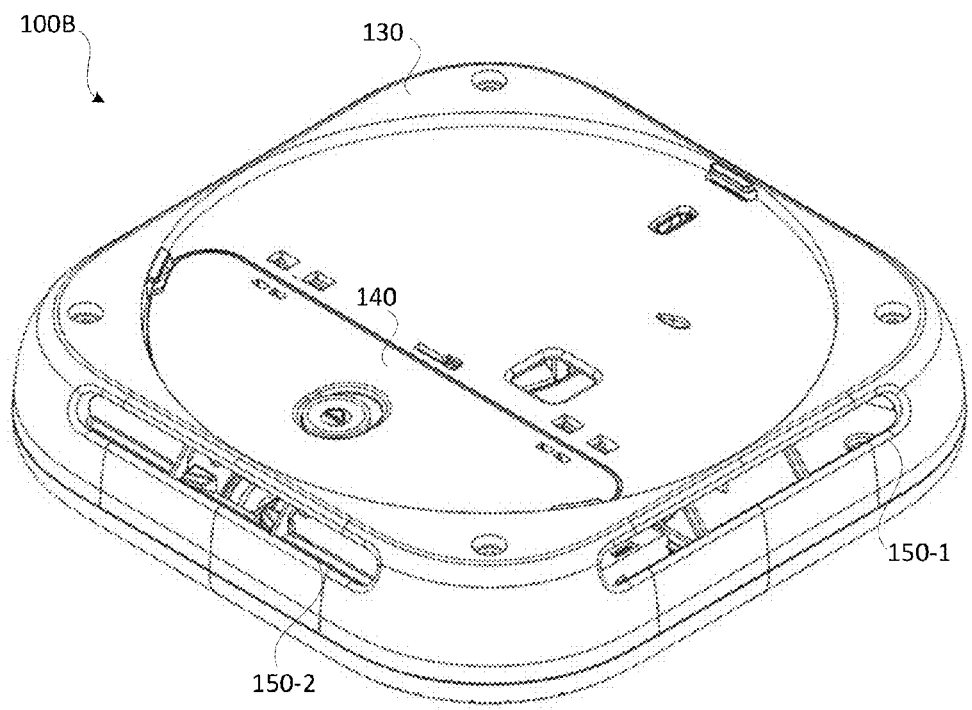

FIG. 1B illustrates an angular bottom projection view of a smart combined smoke detector and carbon monoxide device 100B. It should be understood that device 100A and device 100B may be the same device viewed from different angles. Visible from this view is a portion of enclosure 130. On enclosure 130, battery compartment door 140 is present through which a battery compartment is accessible. Also visible are airflow vents 150-1 and 150-2, which allow air to pass through enclosure 130 and enter the smoke chamber of device 100B.

Figure 2A:
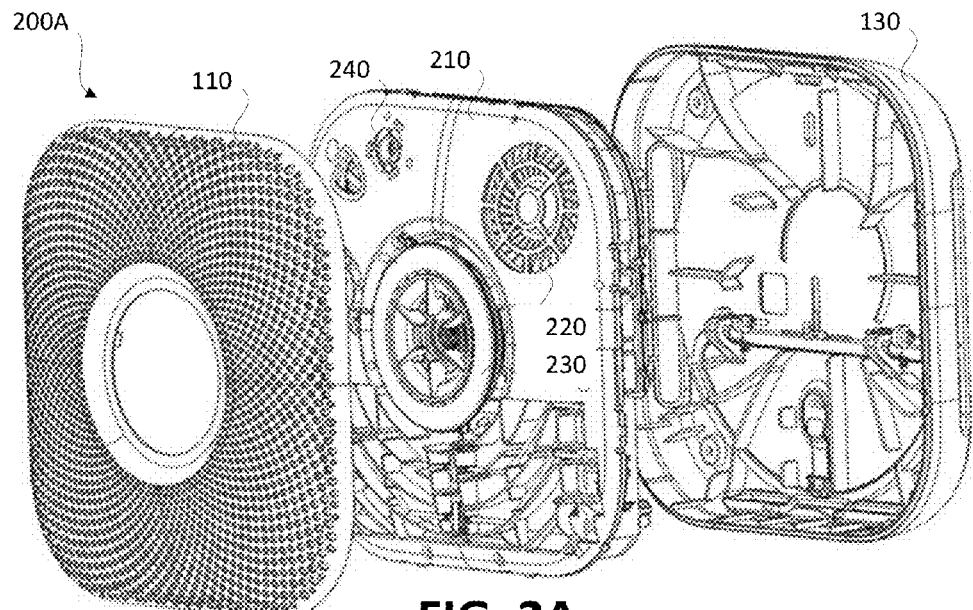
FIGS. 2A, 2B, 2C, and 2D illustrate an embodiment of an exploded smart combined smoke detector and carbon monoxide device.
Figure 2B:
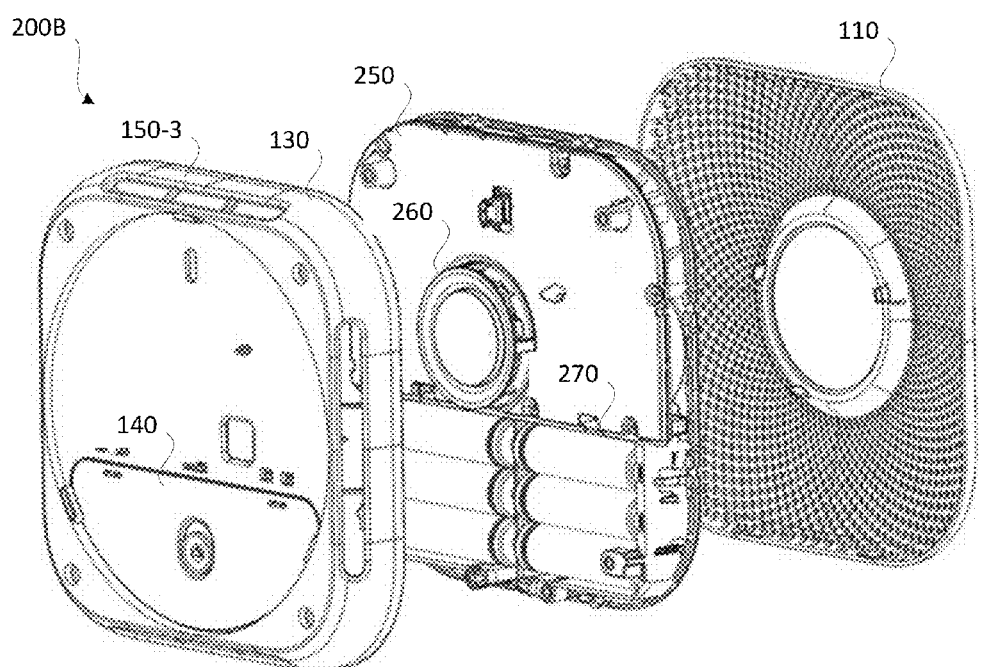
Figure 2C:
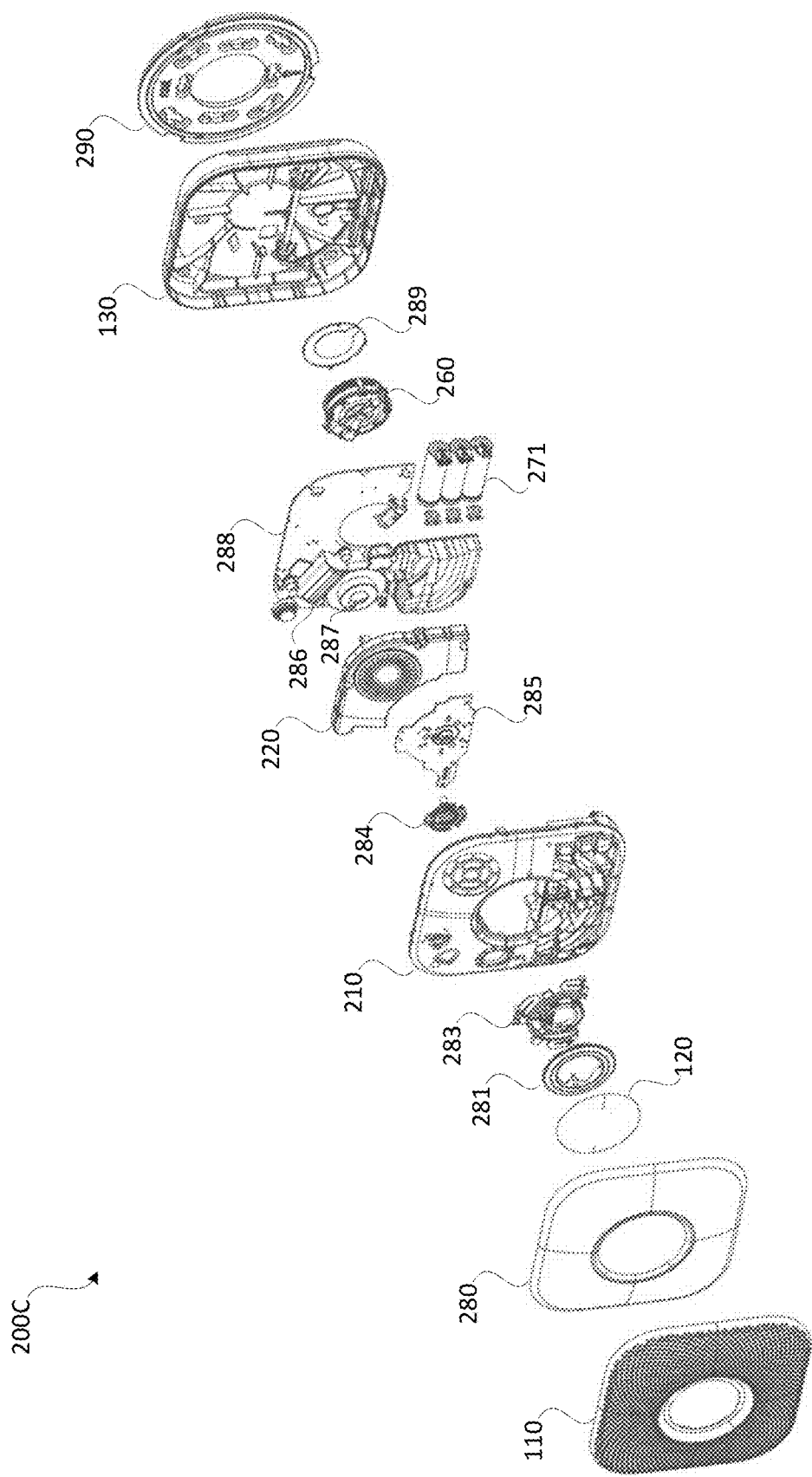

FIGS. 2A, 2B, and 2C illustrate an embodiment of an exploded smart combined smoke detector and carbon monoxide device. The devices of FIGS. 2A-2C can be understood as representing various views of devices 100A and 100B of FIGS. 1A and 1B, respectively. In FIG. 2A, device 200A is shown having cover grille 110 and enclosure 130, which together house main chassis 210. Main chassis 210 may house various components that can be present in various embodiments of device 200A, including speaker 220, light guide 230, and microphone 240. FIG. 2B of an embodiment of device 200B can be understood as illustrating the same device of FIG. 2A, from a different viewpoint. In FIG. 2B, cover grille 110, enclosure 130, airflow vent 150-3, battery compartment door 140 are visible. A gap may be present between enclosure 130 and main circuit board 288 to allow airflow through airflow vents 150 to have a relatively unobstructed path to enter and exit smoke chamber 260. In some embodiments, main circuit board 288 may include one or more laminar flow covers positioned over some or all components of the main circuit board 288 to help with even, laminar airflow within the device and to prevent a user from accidentally touching an electrostatic discharge (ESD) sensitive component. Also present in FIG. 2B are multiple batteries, which are installed within battery compartment 270 of device 200B and which are accessible via battery compartment door 140.

FIG. 2C represents a more comprehensive exploded view of a smart combined smoke detector and carbon monoxide detector device 200C. Device 200C may represent an alternate view of devices 100A, 100B, 200A, and 200B. Device 200C may include: cover grille 110, mesh 280, lens/button 120, light guide 281, button flexure 283, main chassis 210, diaphragm 284, passive infrared (PIR) and light emitting diode (LED) daughterboard 285, speaker 220, batteries 271, carbon monoxide (CO) sensor 286, buzzer 287, main circuit board 288, smoke chamber 260, chamber shield 289, enclosure 130, and surface mount plate 290. It should be understood that alternate embodiments of device 200C may include a greater number of components or fewer components than presented in FIG. 2C.

A brief description of the above noted components that have yet to be described follows: Mesh 280 sits behind cover grille 110 to obscure external visibility of the underlying components of device 200C while allowing for airflow through mesh 280. Light guide 281 serves to direct light generated by lights (e.g., LEDs such as the LEDs present on daughterboard 285) to the external environment of device 200C by reflecting off of a portion of cover grille 110. Button flexure 283 serves to allow a near-constant pressure to be placed by a user on various locations on lens/button 120 to cause actuation. Button flexure 283 may cause an actuation sensor located off-center from lens/button 120 to actuate in response to user-induced pressure on lens/button 120. Diaphragm 284 may help isolate the PIR sensor on daughterboard 285 from dust, bugs, and other matter that may affect performance. Daughterboard 285 may have multiple lights (e.g., LEDS) and a PIR (or other form of sensor). Daughterboard 285 may be in communication with components located on main circuit board 288. The PIR sensor or other form of sensor on daughterboard 285 may sense the external environment of device 200C through lens/button 120.

Buzzer 287, which may be activated to make noise in case of an emergency (and when testing emergency functionality), and carbon monoxide sensor 286 may be located on main circuit board 288. Main circuit board 288 may interface with one or more batteries 271, which serve as either the primary source of power for the device or as a backup source of power if another source, such as power received via a wire from the grid, is unavailable. Protruding through main circuit board may be smoke chamber 260, such that air (including smoke if present in the external environment) passing into enclosure 130 is likely to enter smoke chamber 260. Smoke chamber 260 may be capped by chamber shield 289, which may be conductive (e.g., metallic). Smoke chamber 260 may be encircled by a conductive (e.g., metallic) mesh (not pictured). Enclosure 130 may be attached and detached from surface mount plate 290. Surface mount plate 290 may be configured to be attached via one or more attachment mechanism (e.g., screws or nails) to a surface, such as a wall or ceiling, to remain in a fixed position. Enclosure 130 may be attached to surface mount plate 290 and rotated to a desired orientation (e.g., for aesthetic reasons). For instance, enclosure 130 may be rotated such that a side of enclosure 130 is parallel to an edge of where a wall meets the ceiling in the room in which device 200C is installed.

Figure 2D:
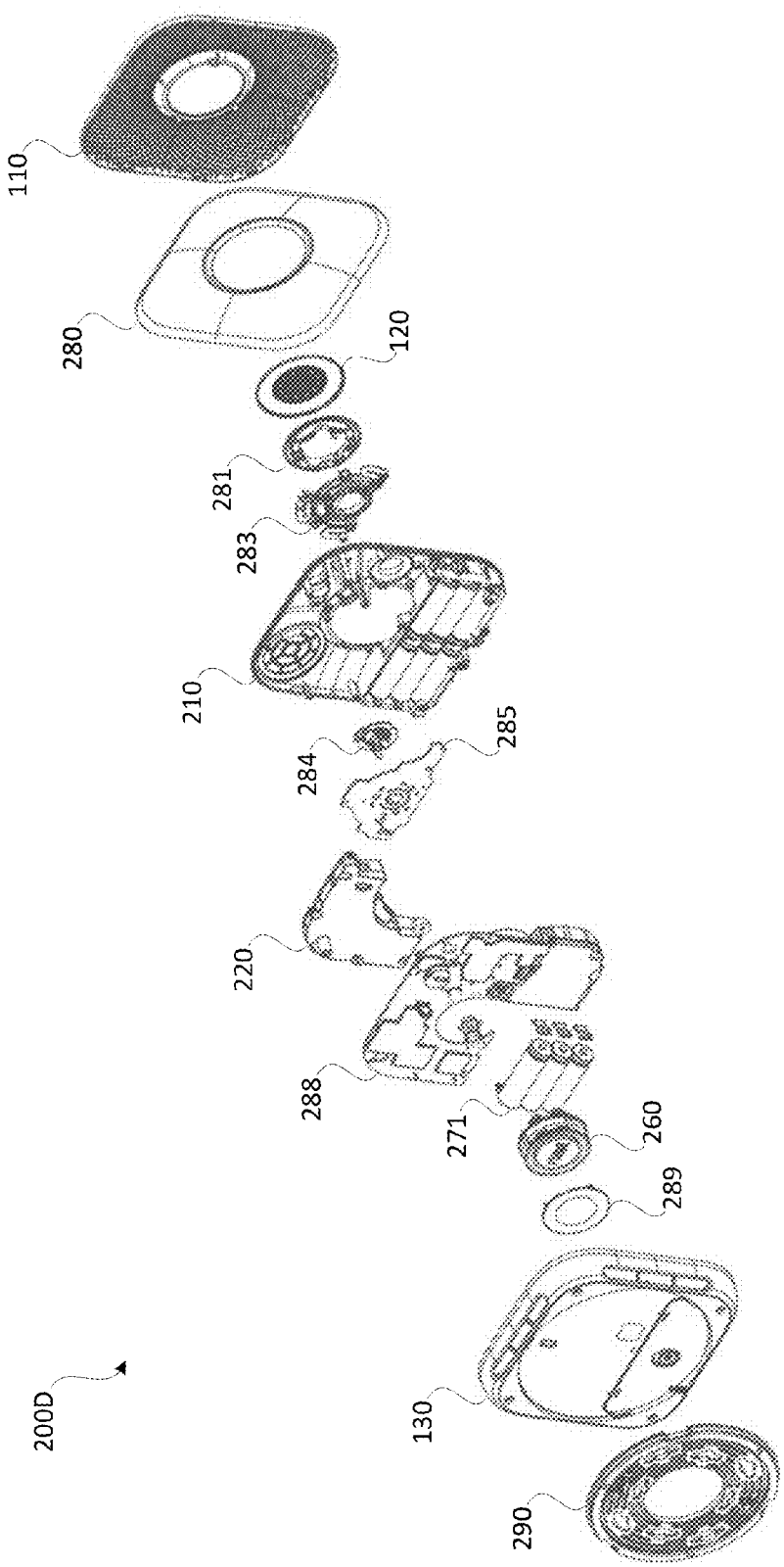

FIG. 2D represents the comprehensive exploded view of the smart combined smoke detector and carbon monoxide detector device of FIG. 2C viewed from a reverse angle as presented in FIG. 2C. Device 200D may represent an alternate view of devices 100A, 100B, 200A, 200B, and 200C. Device 200D may include: cover grille 110, mesh 280, lens/button 120, light guide 281, button flexure 283, main chassis 210, diaphragm 284, passive infrared (PIR) and light emitting diode (LED) daughterboard 285, batteries 271, speaker 220, carbon monoxide (CO) sensor 286, buzzer 287, main circuit board 288, smoke chamber 260, chamber shield 289, enclosure 130, and surface mount plate 290. It should be understood that alternate embodiments of device 200D may include a greater number of components or fewer components than presented in FIG. 2C.

Figure 3:
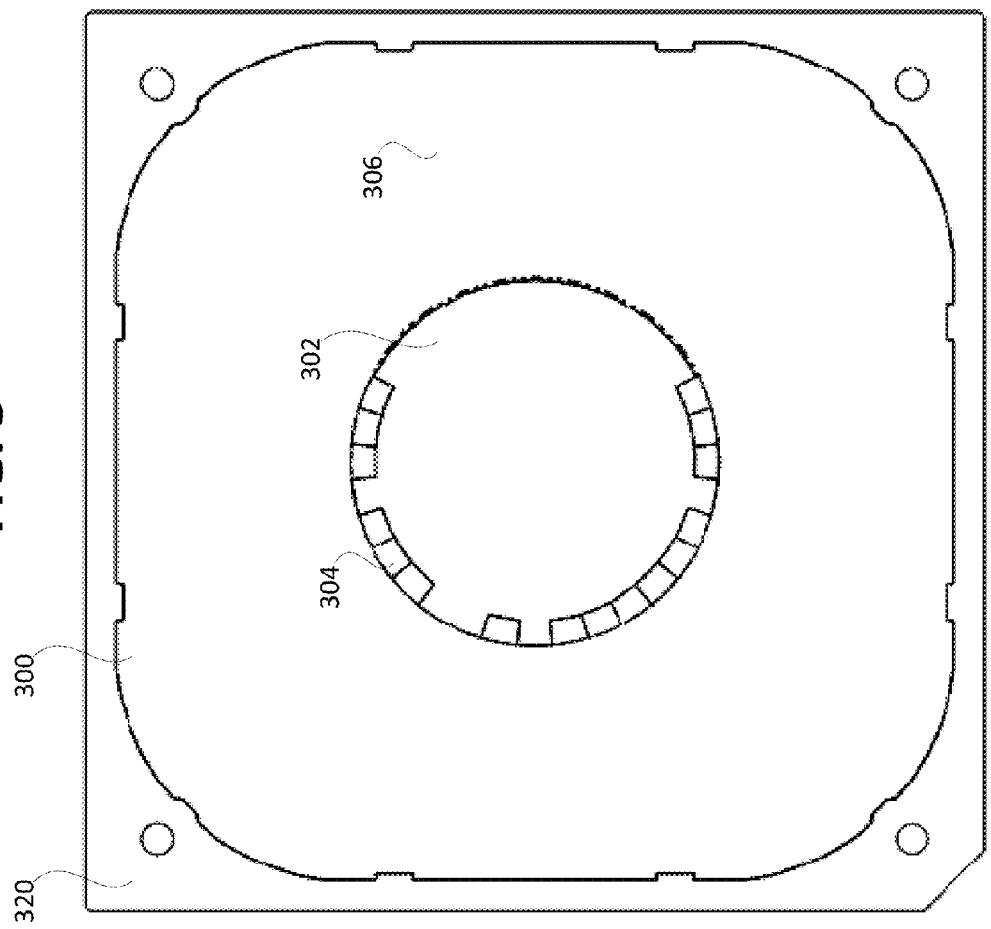
FIG. 3 illustrates a top view of a mesh according to embodiments.

FIG. 3 shows a mesh 300 secured to a release liner 320. The mesh 300 may be the mesh 280 as described in the above figures. Mesh 300 may be shaped to match all or a portion of an interior surface a front surface of a chassis, such as main chassis 210 described above. For example, release liner 320 may be removed to expose an adhesive surface of the mesh 300 that may be secured with one or more of an interior surface of a cover grille or a front surface of a chassis. The adhesive surface may cover all or substantially all of a surface of the mesh 300, or may cover only a portion of the mesh 300, such as tabs 304. The mesh 300 may be aligned with the cover grille and/or the chassis and adhered to the component or components. Heat and/or pressure may be applied to the mesh 300 to mold the mesh 300 to conform to a contour of the matching component, the chassis or the cover grille such that a uniform contoured appearance is provided.

In some embodiments, the mesh contacts all or substantially all of the interior portion of the cover grille and/or the front surface of the chassis. In embodiments where the mesh only covers a portion of the chassis, the mesh 300 may be formed to cover an area defined by a number of apertures formed in a cover grille, such as cover grille 110, which covers the mesh 300 and chassis. In this manner, the portion of the chassis and openings in the chassis that are exposed via the apertures will have a uniform appearance due to the presence of the mesh 300. As shown here, mesh 300 defines a central aperture 302. Central aperture 302 may be included to match corresponding features on the cover grille and/or chassis. For example, the aperture 302 enables the placement of other features of the smoke and carbon monoxide detector or other hazard detector. In some embodiments, the mesh 300 may not include aperture 302, instead presenting a substantially solid profile. The mesh 300 may also include one or more apertures positioned off-center, typically to match a shape of the chassis and/or cover grille. In embodiments having a central aperture 302, a number of flexible tabs 304 may be disposed radially around an inner edge of the mesh 300, such that the tabs 304 extend around at least a portion of an outer periphery of the central aperture 302. Tabs 304 may surround all or substantially all of the outer periphery. The tabs may be spaced apart and have slits or other openings positioned in between the individual tabs 304. The slits may have small widths, such that adjacent tabs are nearly touching, or the openings may be quite large such that noticeable amount of the inner portion of the mesh 300 around the central aperture 302 does not have tabs. Each tab 304 may be flexed or otherwise positioned independent of the other tabs 304. This enables each tab 304 to be flexed to match a contour of the front surface of the chassis positioned adjacent the tab 304. Tabs 304 may be relatively straight fingerlike projections as shown here, or make take other forms. For example, fewer, wider tabs may be provided, the tabs may be in a spiral orientation around the outer periphery of aperture 302, and/or other arrangements may be used. Oftentimes, thinner tabs are used to provide more flexibility. This allows the tabs to be flexed and secured to a front surface of the chassis without causing creases or pinching in the mesh. Some or all of the tabs may be flexed and/or secured to the front surface, providing increased strength of the coupling.

A porous surface 306 of the mesh 300 ensures that some light, such as ambient, ultraviolet, or infrared light, as well as carbon monoxide within the air can pass through to the sensors stored within the chassis. Some amount of light may be sensed by a light sensor. In some embodiments, the light sensor may be used to trigger conditions for a lighting feature of the detector. For example, if the sensor detects that there is little ambient light, a lighting element of the detector may be activated, such as when the detector senses a passing person. Such systems may provide additional or alternative light sources in areas such as hallways and stairwells. Oftentimes, the functionality of the light sensor may depend on the ability to detect a certain range of ambient light, such as between about 0.2 and 1.4 lux in a test box with a known light source. The mesh 300 also has sufficient porosity and acoustic properties such that alarm sounds may be emitted from components of the chassis and be audible at an intensity of at least 85 decibels at a distance of 3 meters from the smoke and carbon monoxide detector in order to meet product safety standards. Typically, a buzzer or speaker produces a signal at between about 3000 and 3500 Hz, although other frequencies may be used based on the needs of a particular application. To achieve the airflow and acoustic results, materials having a porosity between about 5000 and 6500 L/m²s (air permeability) and between 5 and 15 MKS rayls (Specific Airflow Resistance) and between 30 and 40 percent open area may be selected. In some embodiments, the mesh 300 may be formed from woven fibers. In such embodiments, the porosity may be determined based on a combination of fiber size and spacing between fibers. For example, fibers having diameters between about 50 and 75 microns may be spaced apart by between about 100 and 200 microns to achieve the desired porosity. The selection of proper combinations of fiber thickness and spacing creates a percent open area or mesh size that ensures a uniform appearance, while providing desired acoustic and/or permeability characteristics for use in detectors.

In other embodiments, a mesh 300 may be molded as an open mesh and/or formed as a solid piece and then perforated to form openings for light, sound, and carbon monoxide to pass through. In such embodiments, a mesh size creating an open area of between 30 and 40 percent may be used to achieve the desired porosity, acoustic properties, and/or light permeability. A thickness of mesh 300 may also contribute to the porosity and/or light and acoustic properties of the mesh. Oftentimes, the mesh may be between about 75 and 200 microns thick. Additionally, a color of the mesh 300 may be selected to aid in matching ambient light and/or aesthetic characteristics. For example, a black mesh may provide a better appearance, but may block more light. Thus, a combination of porosity, color, fiber diameter, fiber spacing, mesh thickness, and/or a mesh sizing/percent open area may be considered when selecting the material for the mesh 300. The mesh 300 may be formed from any material that provides the necessary. For example, materials such as natural and synthetic fabrics, metallic meshes, silicon meshes, and other natural and/or synthetic meshes may be used to achieve the desired porosity and aesthetic, acoustic, and light effects. One example of a suitable material may be an acoustic mesh No. PE160/64 produced by Shang Hai Yuen Trade Co. Ltd. This mesh has a mesh count of 160 n/inch (thread per inch), a thread diameter of 64 microns, a mesh opening of 92 microns, an open area of 35%, and a thickness of 120 microns. Another suitable mesh is Saati Acoustex 010, having a specific airflow resistance of 10 MKS rayls, a pore size of 130 microns, a thickness of 120 microns, a weight of 100 g/m³. While described having the above properties, it will be appreciated that in applications having larger detector devices, different purposes such as detecting the presence of different substances, and/or different sized openings in the cover grille, and/or other variation materials having different porosities, fiber diameters, spacing, and the like may be used to satisfy the requirements of the particular application.

In some embodiments, the molded mesh 300 may include a molded fabric material. As used herein, fabric refers generally to a material structure of interconnected parts, such as can be formed by knitting, weaving, or felting natural or synthetic fibers, assembling natural or synthetic fibers together into an interlocking arrangement, fusing thermoplastic fibers, or bonding natural or synthetic fibers together with a cementing medium, and further refers to materials having similar textures or qualities as those formed thereby, such as animal membranes or other naturally occurring substances having fabric-like properties (either inherently or by processing), and such as materials generated by chemical processes yielding fabric-like webbings. Preferably, the fabric is visually opaque so as to inhibit viewability of the innards of the hazard detector through the hole pattern in the cover grille, but at the same time sufficiently porous to allow the passing of gasses, such as carbon monoxide, and/or airborne smoke particles therethrough.

Figure 4:
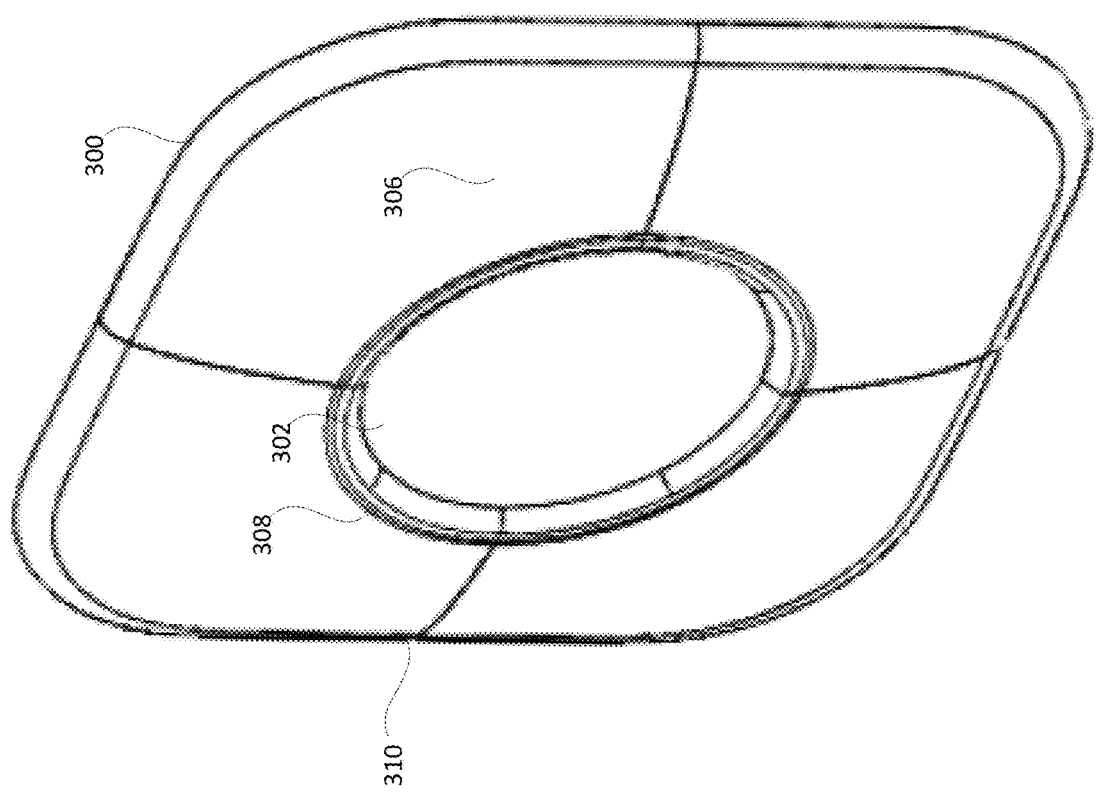
FIG. 4 illustrates an isometric view of the mesh of FIG. 3.

FIG. 4 shows an isometric view of mesh 300. Mesh 300 is three-dimensionally molded such that the mesh 300 has a contour that matches a contour of a front surface of a chassis on which the mesh is to be secured. Here, mesh 300 has a domed contour, where an inner portion 308 of the mesh 300 extends beyond an outer periphery of an outer edge 310 of the mesh 300. While shown as a single, smoothly contouring surface, it will be appreciated that other contours are possible for a mesh. For example, a chassis and/or cover grille may have a channel, bump, ridge, or other three dimensional feature. The mesh 300 may be molded to include a corresponding channel, bump, ridge, or other three dimensional feature. By having a contour matching that of the chassis and/or cover grille, the mesh 300 may sit perfectly or substantially flush or flat against a corresponding surface of the chassis and/or cover grille. This prevents surface imperfections, such as puckering, creases, pinching, and the like from hindering the uniform appearance of the mesh 300 and smoke and carbon monoxide detector or other hazard detector.

Figure 5:
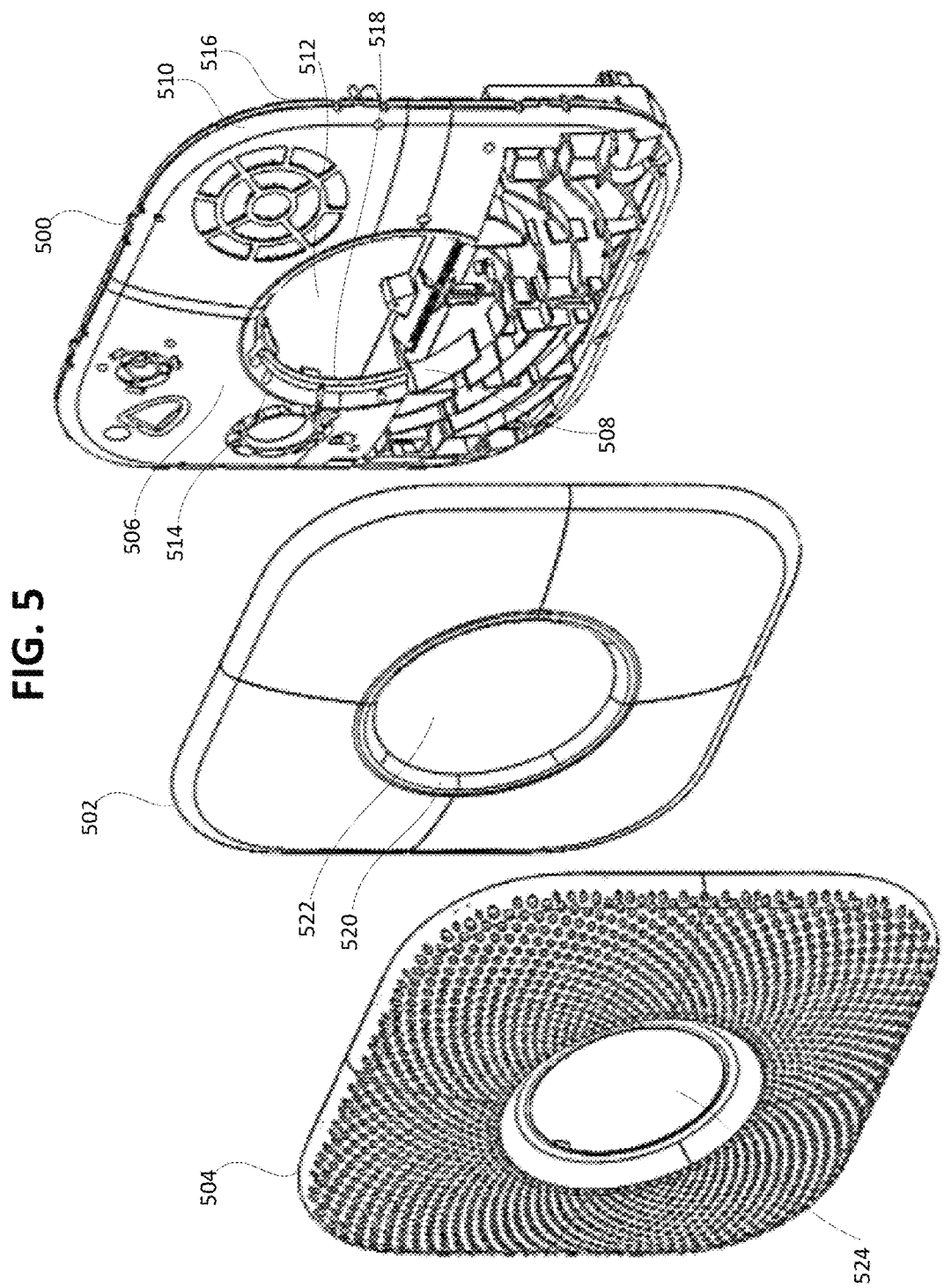
FIG. 5 illustrates an embodiment of an exploded assembly having a chassis, a mesh, and cover grille.

FIG. 5 depicts one embodiment of a chassis 500, mesh 502, and cover grille 504 configured to be coupled to form at least part of a smoke and carbon monoxide detector. Chassis 500, mesh 502, and cover grille 504 may be similar to those described above. Chassis 500 is configured to house components of the smoke and carbon monoxide detector. For example, chassis 500 may house smoke sensors, carbon monoxide sensors, battery connectors, light sensors, speakers, and/or other components of the smoke and carbon monoxide detector or other hazard detector. The chassis 500 may have a front surface 506 having an inner portion 508 and an outer portion 510. The inner portion 508 may define a chassis central aperture 512 such that components, for example light guide 230 described above, may be positioned in or around the chassis central aperture 512. Front surface 506 may have a domed contour such that an outer edge 514 of the inner portion 508 extends beyond an outer periphery or outer edge 516 of the front surface 506. The inner portion 508 may have a taper from the outer edge 514 toward an inner edge 518 of the inner portion 508 near the center of the chassis 500. It will be appreciated that a chassis 500 may have a different arrangement of features and/or a different shape and/or contour than that shown in FIG. 5. For example, an inner portion may be flat, rather than tapered, and/or the inner portion may include multiple contours or surface levels.

Mesh 502 is formed to match a three dimensional shape of the domed contour, or other surface profile, of the front surface 506 of the chassis 500 such that the mesh 502 is substantially flat or flush against the front surface 506 to prevent surface imperfections, especially upon placement of grill 504 over mesh 502. Mesh 502 may be secured to at least a portion of the front surface 506. For example, a number of tabs 520 may project from mesh 502 near a central aperture 522 that is defined by the mesh 502 and corresponds to the chassis central aperture 512. The tabs 520 may be formed radially around at least a portion of the mesh central aperture 522. The tabs 520 may be flexed independent of one another such that each tab 520 may match the taper or other contour of the inner portion 508 of the front surface 506 adjacent to the tabs 520. Some or all of these tabs 520 may be secured to the inner portion of the chassis, such as by using a liquid or tape adhesive, to secure the mesh 502 to the chassis 500. In other embodiments, an adhesive may be applied to the entire or a substantial portion of the front surface 506 and/or the mesh 502.

The mesh 502 may have similar properties as the meshes described herein, such as mesh 300. For example, the mesh 502 may have an air permeability of between about 5000 and 6500 L/m²s and specific airflow resistance of between about 5 and 15 MKS rayls such that an audible signal of approximately 85 decibels may be emitted from the smoke and carbon monoxide detector that is audible at least 3 meters from the smoke and carbon monoxide detector or other hazard detector and such that the molded mesh is penetrable by carbon monoxide or other detectable substance. The mesh 502 may be formed from woven fibers having diameters between about 50 and 75 microns as well as a fiber spacing of between about 100 and 200 microns. Mesh 502 may be between about 75 and 200 microns thick and formed from any natural and/or synthetic material capable of providing the desired acoustic and/or permeability characteristics.

Cover grille 504 may be releasably secured to the chassis 500 such that mesh 504 is disposed between cover grille 504 and chassis 500. For example, the cover grille 504 may be secured to chassis 500 using a snap fit, using threading, press fit, friction fit, or other method of securement. One or both of an outer surface 522 and the inner surface (not shown) of the cover grille 504 may be contoured to match the domed contour, or other surface profile, of the front surface 506 of the chassis 500. In some embodiments, the inner surface of the cover grille 504 contacts the mesh 502. The cover grille 504 may define a grille central aperture 524 corresponding to the chassis central aperture 512 and mesh central aperture 522 to provide access to components such as light guide 230. In other embodiments, the cover grille 504 may define no central or other component apertures. Cover grille 504 does define a number of openings 524 positioned along a body of the cover grille 504. Opening 524 may provide pathways for carbon monoxide, other particulate matter, light, and/or sound to pass between internal components of the smoke and carbon monoxide detector and an environment outside of the smoke and carbon monoxide detector or other hazard detector. In some embodiments, openings 524 may be positioned along an entire body of the cover grille 504, thus providing a uniform appearance. In other embodiments, the openings 524 may be positioned where needed, such as near sensor positions of the chassis 500. This may result in a more random appearance of the openings 524. In some embodiments, the openings 524 may be circular or other-shaped apertures arranged. These apertures may be arranged equidistant from one another or in patterns. Typically uniform and/or symmetrical arrangements of the apertures that create a consistent appearance. The apertures may all have the same diameters and/or sizes, or the diameter and/or size may vary amongst the apertures, such as in a pattern or based on the location of different sensors around the smoke and carbon monoxide detector or other hazard detector. For example, apertures near a speaker may be larger to ensure that sound emitted from the speaker, buzzer, and/or other sound-generating device is sufficiently projected through the cover grille 504, while areas of the cover grille 504 without sensors may have a smaller diameter. Circular apertures may have diameters and spacing to achieve a desired open area percentage. In some embodiments, this open area percentage may be between 30 and 40 percent. In other embodiments, openings 524 may have other shapes, such as linear or curved slits or channels.

Figure 6:
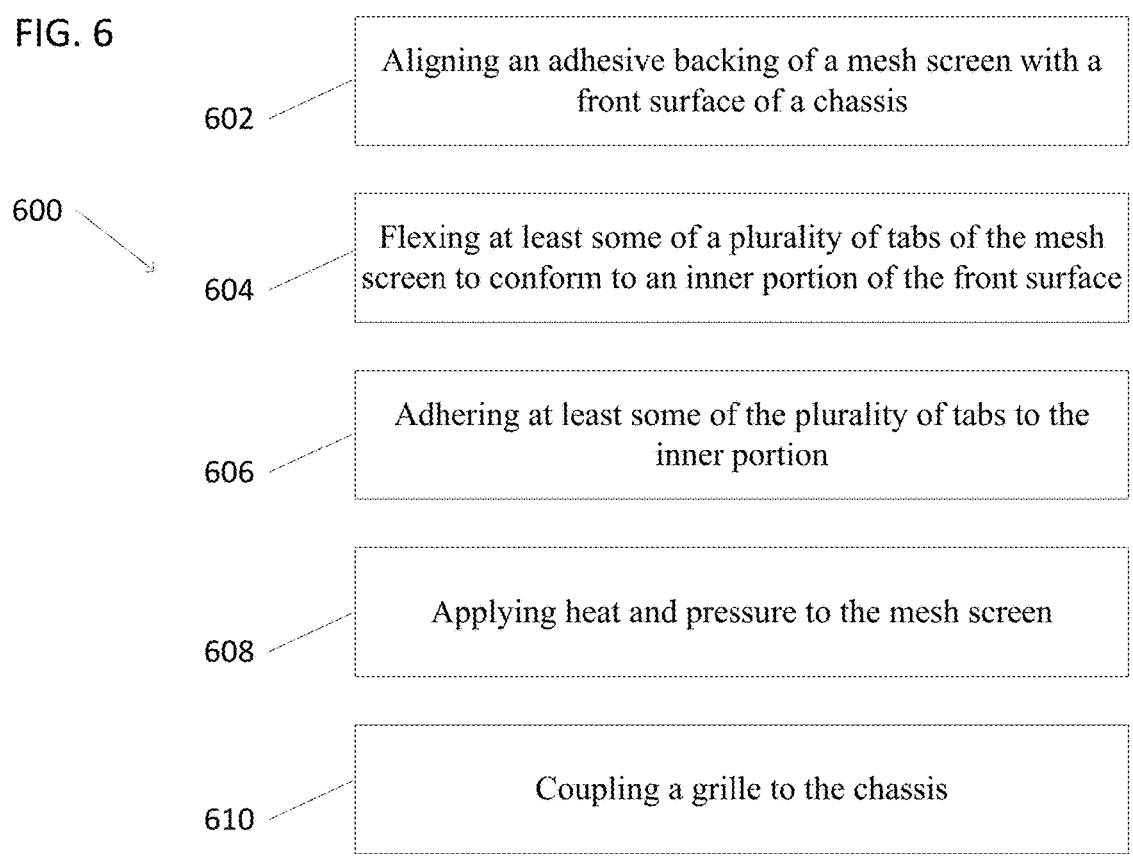
FIG. 6 illustrates a flowchart depicting a process of securing a molded mesh to a chassis of a hazard detector according to embodiments.

FIG. 6 is a flowchart depicting a method 600 of securing a molded mesh to a chassis of a smoke and carbon monoxide detector or other hazard detector. The mesh and detector may be the meshes and detectors described above. An adhesive backing of a mesh may be aligned with a front surface of the chassis at block 602. The chassis may include a chassis central aperture and the mesh may include a corresponding mesh central aperture. A number of tabs may be formed radially around the mesh central aperture. These tabs may be aligned with a tapered inner portion of the front surface of the chassis. The front surface may feature a domed contour such that an outer edge of the tapered inner portion extends beyond an outer periphery of the front surface. The inner surface may include a conically-shaped taper such that the outer edge tapers toward a center of the chassis to an inner edge of the inner portion. At least some of the plurality of tabs may be flexed to conform to the shape of the tapered inner portion at block 604. At block 606, at least some of the plurality of tabs may be adhered to the tapered inner portion such that the mesh is secured to the chassis. This may be done by applying an adhesive, such as a liquid adhesive or a tape adhesive to a mating surface of the tabs and/or the inner surface. In some embodiments, the mesh may have an adhesive portion attached thereto upon manufacture. Oftentimes, a release liner may be included such that when removed, an adhesive portion is exposed. The mesh may then be positioned against the front surface. In some embodiments, the mesh may include an adhesive portion or an applied adhesive on all or substantially all of the front surface of the chassis and/or the mesh. This can provide a larger, stronger bonding surface, although alignment for subsequent molding may be more difficult as the larger area of adhesive may tend to bunch up.

Heat and pressure may be applied to the mesh to mold the mesh to conform to the domed contour of the front surface at block 608. This may be done, for example, by pressing a heated mold against the mesh and the chassis. Exposure to the heated mold may result in a rearrangement of the fibers of the mesh such that the mesh may take on the three-dimensional contours of the front surface. As such, pinching, wrinkling, and the like are eliminated, even in areas of curved topography. The heated mold may be formed from a conductive material, such as copper or another metal alloy. An interior surface of the heated mold may have a contour matching the domed contour of the front surface such that the mesh is molded to conform to the domed contour. The heated mold may be heated to between about 70 and 90° C. The headed mold may be pressed against the mesh and the chassis for between about 5 and 15 seconds at a pressure of between about 2 and 5 kgf/cm². A proper amount of temperature, pressure, and/or time of application of the heat and pressure is should be used in accordance with the present teachings, such that mesh will hold the proper shape. Where the temperature, pressure, and/or time is properly kept from being excessive in accordance with the present teachings, adverse or undesirable fusing together of the woven fibers is avoided and any associated undesirable aesthetics, acoustics, or poor/inconsistent porosities are avoided. As such, proper fabrication according to the present teachings maintains sufficient porosity such that carbon monoxide, smoke particles, or other noxious substances of interest will properly pass through the mesh and reach the appropriate sensors, while at the same time a visually pleasing aesthetic formed by the cover grille and its associated hole pattern is provided.

It will be appreciated that many structural features of the chassis, cover grille, and mesh may be varied in accordance with the invention. For example, the central apertures may be omitted or positioned off-center, the interior of the cover grille may not conform to a contour of the chassis, and/or other alterations may be made. The mesh may be configured to provide a consistent appearance, while ensuring that the assembly and operation of the detector is maintained.

What is claimed is:

1. A hazard detector comprising:
    a chassis;
    one or more hazard sensors housed within the chassis;
    a grille that defines a plurality of holes, wherein an inner surface of the grille has a three-dimensional contour and the grille is secured to the chassis; and
    a porous mesh that is formed to match the three-dimensional contour of the inner surface of the grille, the porous mesh being positioned against the inner surface of the grille, wherein the porous mesh obscures viewing, through the plurality of holes, of internal componentry of the hazard detector.

2. The hazard detector of claim 1, wherein the chassis comprises a three-dimensionally contoured front surface and the porous mesh is positioned between a front surface of the chassis and the inner surface of the grille.

3. The hazard detector of claim 1, wherein the porous mesh is molded in a three-dimensional shape.

4. The hazard detector of claim 1, wherein:
    the chassis further defines an aperture, larger than a hole of the plurality of holes; and
    the aperture is at least partially encompassed by a conically-shaped surface of the chassis.

5. The hazard detector of claim 4, wherein the porous mesh defines a mesh central aperture corresponding to the aperture of the chassis and the porous mesh comprises a plurality of flexible tabs formed radially at least partially around the mesh central aperture.

6. The hazard detector of claim 5, wherein at least some of the plurality of flexible tabs are secured to the conically-shaped surface of the chassis.

7. The hazard detector of claim 1, wherein the porous mesh comprises woven fibers having diameters between about 50 and 75 microns.

8. The hazard detector of claim 7, wherein the woven fibers are spaced apart by between about 100 and 200 microns.

9. The hazard detector of claim 1, wherein the grille has a domed contour.

10. The hazard detector of claim 1, wherein the porous mesh has an air permeability of at least 5000 L/m$^2$s such that an audible signal of approximately 85 decibels may be emitted from the hazard detector that is audible at least 3 meters from the hazard detector and such that the porous mesh is penetrable by a particulate matter detectable by a hazard sensor of the one or more hazard sensors of the hazard detector.

11. A method of securing a porous mesh of a hazard detector, the method comprising:
    aligning the porous mesh with a front surface of a chassis;
    flexing a plurality of tabs of the porous mesh to conform to a portion of the chassis;
    adhering the plurality of tabs to the portion of the chassis such that the porous mesh is secured to the chassis;
    applying heat and pressure to the porous mesh to mold the porous mesh to conform to a three dimensional shape of the front surface of the chassis; and
    coupling a grille to the chassis, such that the mesh is disposed between the grille and the chassis and the porous mesh obscures view through a plurality of holes of the grille of internal componentry of the hazard detector.

12. The method of securing the porous mesh to the chassis of the hazard detector of claim 11, wherein applying heat and pressure to the porous mesh comprises:
    pressing a heated mold against the porous mesh, a surface of the heated mold having a contour conforming to the three-dimensional shape of the front surface of the chassis such that the porous mesh is molded to conform to the three-dimensional shape.

13. The method of securing the porous mesh to the chassis of the hazard detector of claim 12, wherein:
    the heated mold is heated to between about 70 and 90° C. and is pressed against the porous mesh and the chassis at a pressure of between about 2 and 5 kgf/cm$^2$.

14. The method of securing the porous mesh to the chassis of the hazard detector of claim 11, wherein the porous mesh has an air permeability of between about 5000 and 6500 L/m$^2$s.

15. The method of securing the porous mesh to the chassis of the hazard detector of claim 11, wherein:
    the porous mesh comprises woven fibers have diameters between about 50 and 75 microns; and
    the woven fibers are spaced apart by between about 100 and 200 microns.

16. The method of securing the porous mesh to the chassis of the hazard detector of claim 11, wherein:
    the porous mesh has a thickness between about 75 and 200 microns.

17. A hazard detector comprising:
    a chassis configured to house components of the hazard detector;
    a grille secured to the chassis, the grille defining a plurality of openings, wherein an inner surface of the grille comprises a three-dimensional contour;
    a three-dimensionally molded porous mesh secured against the inner surface of the grille, wherein:
    the three-dimensionally molded porous mesh conforms to the three-dimensional contour of the inner surface of the grille such that the three-dimensionally molded porous mesh lies flat against the inner surface of the grille; and
    the three-dimensionally molded porous mesh comprises woven fibers having diameters between about 50 and 75 microns, the woven fibers spaced apart from one another by between about 100 and 200 microns.

18. The hazard detector of claim 17 wherein the three-dimensionally molded porous mesh has an air permeability of at least 5000 L/m$^2$s.

19. The hazard detector of claim 18 wherein an audible signal of approximately 85 decibels is emitted from the hazard detector that is audible at least 3 meters from the hazard detector.

20. The hazard detector of claim 19 wherein the three-dimensionally molded porous mesh is penetrable by particulate matter detectable by a hazard sensor of the hazard detector.

* * * * *